(12) United States Patent
Lechocinski et al.

(10) Patent No.: US 7,986,401 B2
(45) Date of Patent: Jul. 26, 2011

(54) BIREFRINGENT FIBERS ORIENTATION MEASUREMENT

(75) Inventors: Nicolas Lechocinski, Los Angeles, CA (US); Sebastien Breugnot, Los Angeles, CA (US); Bruno Francois Pouet, Los Angeles, CA (US)

(73) Assignee: Bossa Nova Technologies, LLC, Venice, CA (US)

( * ) Notice: Subject to any disclaimer, the term of this patent is extended or adjusted under 35 U.S.C. 154(b) by 130 days.

(21) Appl. No.: 12/567,579

(22) Filed: Sep. 25, 2009

(65) Prior Publication Data
US 2011/0075128 A1 Mar. 31, 2011

Related U.S. Application Data

(60) Provisional application No. 61/192,702, filed on Sep. 22, 2008.

(51) Int. Cl.
*G01N 21/00* (2006.01)
(52) U.S. Cl. .................................... 356/73.1

(58) Field of Classification Search .................. None
See application file for complete search history.

(56) References Cited

U.S. PATENT DOCUMENTS 6,611,369 B2 * 8/2003 Matsushita et al. ........... 359/334
7,289,210 B2 * 10/2007 Jang .............................. 356/364

* cited by examiner

*Primary Examiner* — Tu T Nguyen
(74) *Attorney, Agent, or Firm* — Osha Liang LLP

(57) ABSTRACT

Methods and apparatus to determine the orientation of randomly arranged birefringent fibers are disclosed. One method comprises emitting light, creating $N_i$ polarization states of the emitted light, illuminating the birefringent fibers with the emitted light so polarized, thereby generating $IR_i$ internal reflection components of the light in the birefringent fibers, observing the light from the illuminated birefringent fibers, creating $O_i$ polarization states of the observed light, forming $I_i$ images of the observed polarized light, each image comprising an information $(N_i, O_i, IR_i)$, wherein $i=1, 2, \ldots, n$ and $n \geq 3$, separating the i-th internal reflection component from the i-th image, and calculating an angle of a neutral axis of the birefringent fibers using the $IR_i$ internal reflection components.

17 Claims, 6 Drawing Sheets

With 90° ambiguity

Without ambiguity

1

BIREFRINGENT FIBERS ORIENTATION MEASUREMENT

CROSS-REFERENCE TO RELATED APPLICATIONS

The present application claims priority under 35 U.S.C. §119(e) to U.S. Provisional Patent Application Ser. No. 61/192,702, entitled "Visual appearance measurement method and system for randomly organized birefringent fibers" filed on Sep. 22, 2008 by Nicolas Lechocinski, et al.

BACKGROUND

1. Field of the Disclosure

The present disclosure relates generally to an apparatus and a method for determining the orientation of randomly arranged birefringent fibers, such as for example textile fibers and hair.

2. Background Art

Polarization imaging is being used in many applications. In passive imaging, where the illumination is not controlled, i.e., not actively polarized, polarization imaging can be used, for example, to enhance the contrast between human made objects that have a strong polarization signature from the natural background. It also provides information on the shape of the objects. Further, polarization imaging conveniently allows for the detection of water or mud surfaces thanks to the strong polarization signature of water.

In active imaging, where the illumination is controlled and polarized, polarization imaging can be used to study light scattering. In fact, two-state polarization allows to easily separate the surface scattering from the volume scattering. Specular reflections and color information can therefore be separated, thus providing information on the structure of the studied objects.

Polarization imaging is applied, for example, in the cosmetic industry where studying the visual appearance (of the skin, the hair, etc.). Polarization imaging can be used as a tool to improve formulation for both hair and skin care products, such as styling products, for example by visualizing the improvement of the structure and appearance of hair once the product is applied.

For determining the orientation of birefringent fibers, such as hair, methods using image processing are known. These methods apply a Fourier transform to the fiber images so as to obtain the orientation of the neutral axis of the fibers. However, according to these methods assumptions have to be made about the light that is internally reflected inside the fibers. Furthermore, in order to obtain the orientation of their neutral axis, the fibers all have to have the same orientation.

Therefore, there is a need to provide an improved method and an improved apparatus for the orientation determination of randomly arranged birefringent fibers which are capable of determining the orientation of the fibers, independently from the orientation thereof.

SUMMARY OF THE CLAIMED SUBJECT MATTER

In a first aspect, the present disclosure relates to a method for determining the orientation of randomly arranged birefringent fibers. The method comprises emitting light, creating $N_i$ polarization states of the emitted light, illuminating the birefringent fibers with the emitted light so polarized, thereby generating $IR_i$ internal reflection components of the light in the birefringent fibers, observing the light from the illuminated birefringent fibers, creating $O_i$ polarization states of the observed light, forming $I_i$ images of the observed polarized light, each image comprising an information ($N_i$, $O_i$, $IR_i$), wherein i=1, 2, ..., n and n≧3, separating the i-th internal reflection component from the i-th image, and calculating an angle of a neutral axis of the birefringent fibers using the $IR_i$ internal reflection components.

Preferably, the birefringent fibers comprise one of textile fibers and hair.

Preferably, the wavelength of the emitted light is in the near infrared range.

According to an alternative preferred embodiment, the wavelength of the emitted light is in the visible range.

Preferably, the i-th polarization state of the emitted light and the i-th polarization state of the observed light are the same.

According to an alternative preferred embodiment, the i-th polarization state of the emitted light is different from the i-th polarization state of the observed light.

Preferably, the calculating comprises performing a Fourier transform on the $IR_i$ internal reflection components in each pixel of the $I_i$ images.

In a second aspect, the present disclosure relates to an apparatus for determining the orientation of randomly arranged birefringent fibers. The apparatus comprises a light source for emitting light, a first variable polarizer for creating $N_i$ polarization states of the emitted light, the emitted light so polarized being indented to illuminate the birefringent fibers, thereby generating $IR_i$ internal reflection components of the light in the birefringent fibers, a detector for observing the light from the illuminated birefringent fibers, a second variable polarizer for creating $O_i$ polarization states of the observed light, wherein the detector is intended to form $I_i$ images of the observed polarized light, each image comprising an information ($N_i$, $O_i$, $IR_i$), wherein i=1, 2, ..., n and n≧3, an image processing unit intended to separate the i-th internal reflection component from the i-th image, and a processor intended to calculate an angle of a neutral axis of the birefringent fibers using the $IR_i$ internal reflection components.

The light source may, for example, comprise a pulsed laser source, a cw laser source, at least one light emitting diode, or a flash lamp.

Preferably, the detector comprises a video camera.

Preferably, each one of the first and the second variable polarizers is actively controlled. However, passively controlled polarizers may also be used. Combinations of actively and passively controlled polarizers may also be envisaged.

Preferably, the first and the second variable polarizers are integrally formed. In other words, the first and the second variable polarizers may be incorporated in a single unit.

Preferably, the image processing unit and the processor are incorporated in a computer.

Preferably, the apparatus further comprises a synchronization unit configured to synchronize the first and second variable polarizers and the detector.

Other aspects, characteristics, and advantages of the invention will be apparent from the following detailed description.

DETAILED DESCRIPTION

Figure 1:
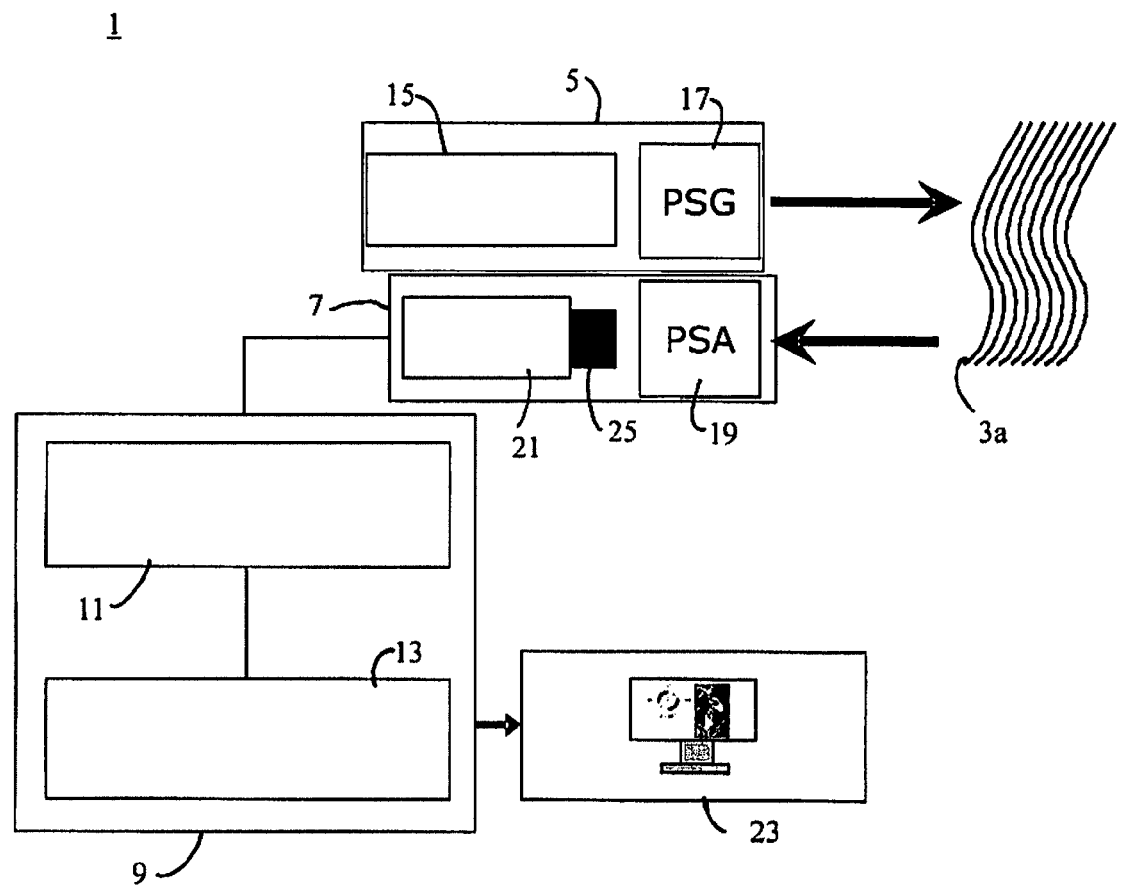
FIG. 1 schematically shows an apparatus for the orientation determination of randomly arranged birefringent fibers according to a preferred embodiment of the present disclosure.

Specific embodiments of the present disclosure will now be described in detail with reference to the accompanying Figures. Like elements in the various Figures are denoted by like reference numerals for consistency.

In general, embodiments of the present disclosure relate to apparatus and method for determining the orientation of randomly arranged birefringent fibers. More specifically, embodiments of the present disclosure provide methods and apparatus for determining the orientation of the neutral axis of birefringent fibers.

We will describe preferred methods and apparatus for the orientation determination of randomly arranged birefringent fibers using a polarization analysis technique. This technique is based on the polarization signature of internal reflections in birefringent fibers. The birefringent fibers may be, for example, human hair or textile fibers, such as for example Nylon fibers or any other birefringent translucent fibers.

FIG. 1 schematically shows an apparatus 1 for the orientation determination of birefringent fibers 3a according to a preferred embodiment of the present disclosure. The birefringent 3a fibers are randomly arranged, and no control of their organization is performed. The apparatus 1 comprises a light source 15, a polarization state generator (PSG) 17, a polarization state analyzer (PSA) 19 and a detector. The light source 15 and the PSG 17 may be parts of a polarization illumination system 5, and the PSA 19 and the detector may be parts of a polarization imaging system 7. The detector is preferably a video camera 21 comprising an objective lens 25. The video camera 21 may be for example a monochrome camera. The light source 15 may be a pulsed or a continuous wave (cw) laser source, one or a plurality of light emitting diodes (LED), a flash lamp, etc. The wavelength of the light source is preferably chosen according to the type of fibers that are measured, i.e., their color and/or their absorption coefficient. For example, for human hair, the wavelength preferably ranges from the visible spectrum to the near infra-red.

The apparatus 1 further comprises a control unit 9, such as a personal computer. The control unit 9 may comprise an image acquisition unit 11, an image processing unit 13, and a processor (not shown). However, the image acquisition unit 11 may also be separate from the control unit 9.

The PSG 17 and the PSA 19 preferably comprise a first and a second variable polarizer, respectively. The PSG 17 and the PSA 19 may comprise actively or passively controlled polarizing components. For example, they may comprise electronically controllable liquid crystals or conventional polarization components positioned on a rotation stage that is rotated mechanically.

Further, the apparatus 1 may comprise a black screen 27 that is adapted to eliminate any parasite reflection on the fibers 3a.

Figure 2:
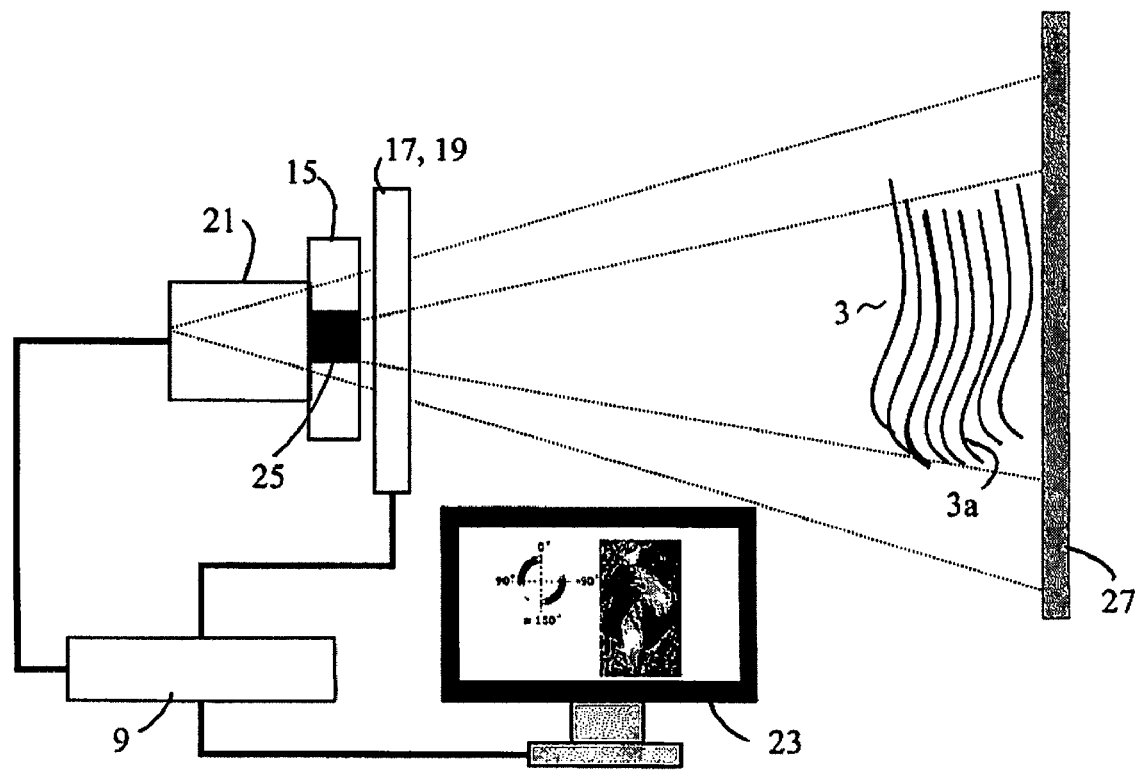
FIG. 2 shows a schematic view of a further preferred embodiment of the present disclosure.

FIG. 2 shows an example setup of the orientation determination apparatus 1. In this embodiment, an illumination and an observation system are arranged in a monostatic configuration, i.e., they share the same optical axis. Other configurations, depending on user-specific requirements, are also possible. The light source 15 consists of a ring of LEDs arranged around the objective lens 25 of the video camera 21. The LEDs may emit light, for example, at a wavelength of 850 nm. The polarization state of the emitted light is set by the PSG 17. The PSG 17 is preferably a NIR linear polarizer mounted on a rotation stage in front of the LEDs. In the example of FIG. 2, the PSG 17 and the PSG 19 form a single unit. A bundle 3 of birefringent fibers 3a is illuminated by the polarized incident light.

Figure 3:
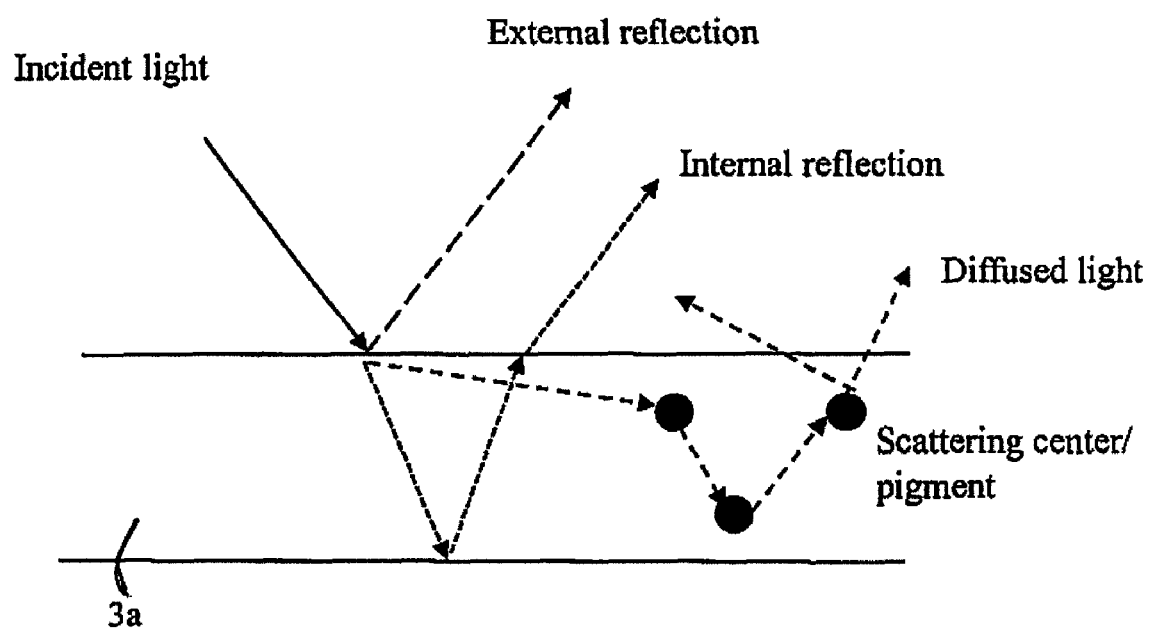
FIG. 3 shows a model of light interaction with a single translucent fiber.

The light reflected by the birefringent fibers contains components from the different interactions of the light with the fibers. The three components that may be observed are the following:
  light coming from the external reflection, i.e., light that is reflected on the external surface of the fiber. The externally reflected light has the same wavelength (color) as the incident light.
  light coming from the internal reflection on an internal surface of the fiber. Since this component propagates through the fiber, it experiences a change of wavelength.
  diffused light from volume scattering inside the fiber.
This general situation is depicted in FIG. 3 with a single fiber 3a.

In the case of polarized incident light, the externally reflected light remains polarized with the same polarization, the internally reflected light becomes elliptically polarized, and the diffused light becomes depolarized.

If the incident light is polarized, two cases may be distinguished:
  i) the polarization state of the incident light is linear and parallel to a neutral axis of birefringence of the fibers, and
  ii) the polarization state of the incident light is such that there is the projections of the polarization components on the neutral axis and the axis perpendicular to it are equal. For example, the incident light may be circularly polarized or linearly polarized with an orientation at 45° with respect to the neutral axis of the fiber).

Figure 4A:
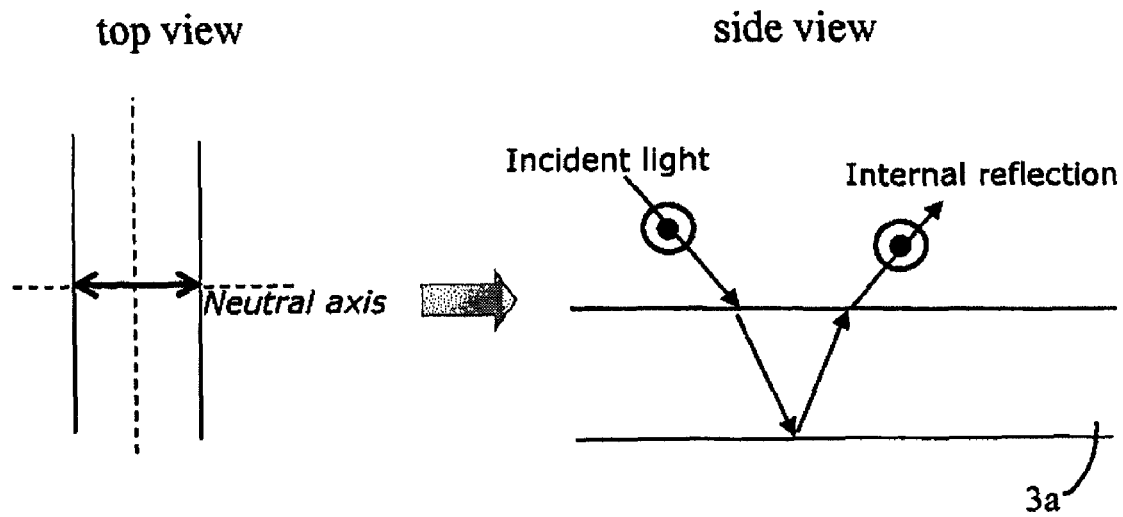
FIG. 4a schematically shows a top view and a side view of a model of internally reflected light in a single fiber for incident light of which the polarization direction is parallel to the neutral axis of the fiber.

Case i) is schematically shown in FIG. 4a. The polarization state of the light is not modified while propagating through the fiber. Thus, the internally reflected light component is completely polarized and its polarization state is preserved.

Figure 4B:
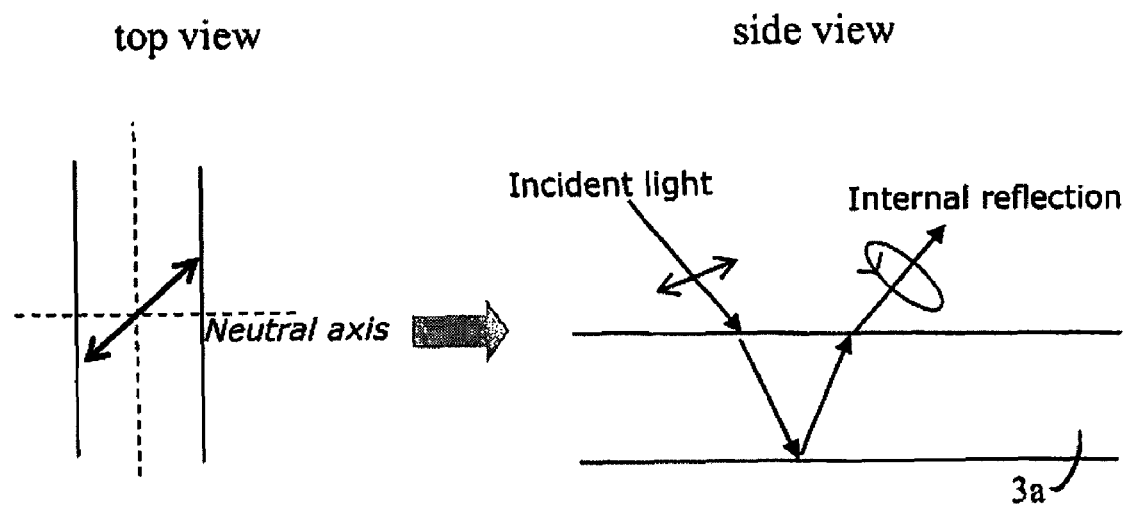
FIG. 4b schematically shows a top view and a side view of a model of internally reflected light in a single fiber for incident light of which the polarization direction is at 45° to the neutral axis of the fiber.

Case ii) is schematically shown in FIG. 4b. The different amount of birefringence experienced by the different polarization components mixed together makes that the light from the internal reflection is circularly polarized.

If the incident light is polarized otherwise than in cases i) and the internally reflected light will be elliptically polarized.

According to the present disclosure, the orientation of randomly organized birefringent fibers is determined using an apparatus as shown in FIG. 1. As shown in the embodiment of FIG. 2, the light coming from the fiber bundle 3, containing the three components external reflection, internal reflection, and diffusion as described above, is detected by the imaging system 7. The observed light first passes through the PSA 19 before entering the objective lens 25 of the video camera 21.

The intensity of the observed light measured this way depends on the state of the polarization analyzer 19. Preferably, the intensity measurement of the light coming from the fiber bundle 3 is realized by taking images of the fiber bundle with the video camera 21 at a given video frame rate. The video camera 21 is controlled by the image acquisition unit 11. The apparatus 1 according to the present disclosure may further comprise one or a plurality of filters in front of the detector that is/are adapted to reject undesired wavelengths, or in front of the light source 15 in order to select an emission wavelength of the light source 15.

As an example, two cases may be distinguished:
(a) the PSG 17 and the PSA 19 are in the same state, i.e., the incident light and the detected light have parallel polarization, or
(b) the PSG 17 and the PSA 19 are in crossed states, i.e., the polarization of the incident light is orthogonal to the polarization of the detected light.

In the case of parallel polarization for illumination and observation (case (a)), the intensity signal $I_\parallel$ detected by the imaging system 7 may be written as:

$$I_\parallel = S + \frac{D}{2} + \beta C, \quad (1)$$

wherein S, C, and D designate the external reflection component, the internal reflection component, and the diffusion component, respectively, and β is the modulation amplitude of the internal reflection component C. It is supposed that the internal reflection is due to a refraction of the incident light on the surface of a fiber followed by a single reflection on the inner surface of the fiber, and further followed by another refraction of the light exiting the fiber. Incident light polarized at 0° with respect to the neutral axis of the fiber experiences a coefficient of refraction that is lower than that for light polarized at 90°, and incident light polarized a 0° is reflected in a greater proportion than light polarized at 90°. Thus, the entrance and exit refractions favor light polarized at 90° while the internal reflection favors light polarized at 0°. If the refraction and internal reflection processes do not compensate each other exactly, the internal reflection is stronger for one of the two polarization states of the incident light.

Figure 5A:
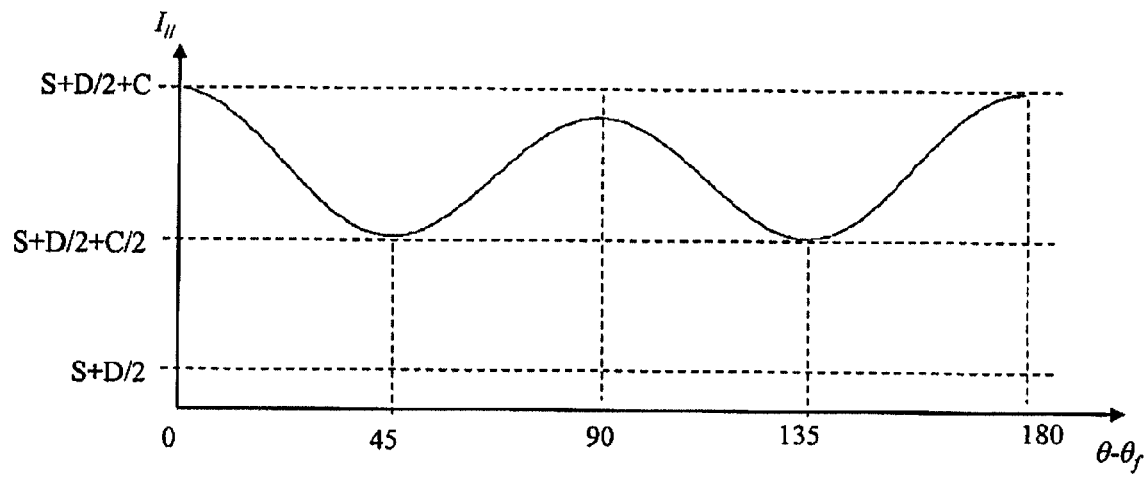
FIGS. 5a and 5b show graphs of measured intensities using the apparatus according to the present disclosure in the case of parallel polarization for illumination and observation and in the case of crossed polarizations for illumination and observation, respectively.

The internal reflection modulation amplitude can be described by the following equation:

$$\beta = \frac{3}{4} + \frac{1}{4}\cos(4(\theta - \theta_f))[1 - M\cos(2(\theta - \theta_f))], \quad (2)$$

wherein M takes into account the dependence of the internal reflection on the polarization state of the incident light, θ is the polarization angle of the incident light, and $\theta_f$ the orientation of the neutral axis of the fiber. The polarization angles θ are set with respect to 0° which is chosen arbitrarily. FIG. 5a shows the variation of $I_{81}$ versus $\theta - \theta_f$.

In the case of crossed polarizations for illumination and observation (case (b)), the intensity signal $I_\perp$ detected by the imaging system may be written as $$I_\perp = \frac{D}{2} + (1 - \beta)C, \quad (3)$$

Figure 5B:
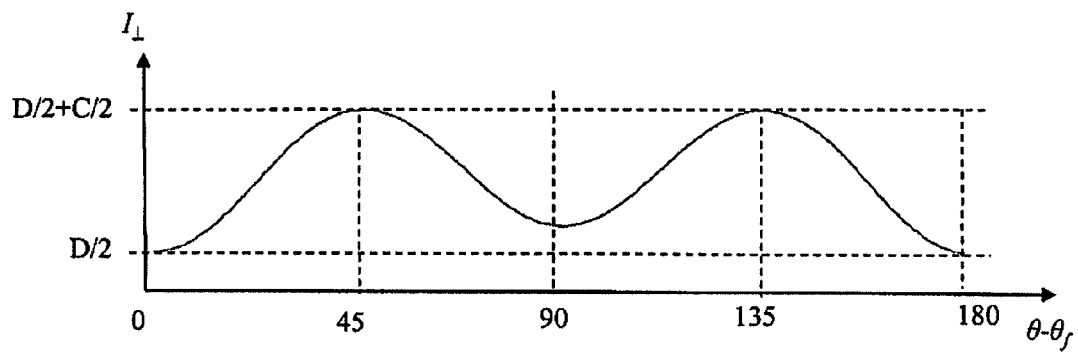

FIG. 5b shows the variation of $I_\perp$ versus $\theta - \theta_f$.

According to the present disclosure, N images are acquired corresponding to N couples of polarization states ($PSG_N$, $PSA_N$). Preferably, N≧3. For example, in parallel configuration ($PSG_N$=$PSA_N$, case (a) described above), the orientation of polarization is 360°/N for the corresponding image. Any other couples and combinations of couples of ($PSG_N$, $PSA_N$) may be employed, whereby the couples need to be different from each other for the N image acquisitions. In the case that the PSG and the PSA are a single piece, the parallel configuration is used. For each pixel (x, y) in the image plane of the N acquired images, a modulated, sinusoidal signal containing N values corresponding to the internal reflection component is obtained using the image processing unit 13.

Since the polarization angle θ, i.e., the state of the PSG, is known for each of the N image acquisitions, the orientation of the neutral axis of the fiber $\theta_f$ for each pixel (x, y) is calculated. Preferably, a signal ($I_{81}$ or $I_\perp$) containing N points for each pixel from the N images is subjected to a Fourier transform in order to obtain the phase of the modulated sinusoidal signal, and thus the angle $\theta_f$ of the neutral axis of the fiber.

If N=3, $\theta_f$ is obtained with an ambiguity of π/2. If N≧6, $\theta_f$ is obtained without ambiguity. Preferably, color-coded orientation images of the fiber bundle indicating the value of $\theta_f$ in each pixel may be output by an output device 23, as shown in FIG. 1 or 2. The output device 23 may comprise, for example, a screen of a personal computer or a printer.

The synchronization of the elements of the apparatus according to the present disclosure is carried using a synchronization unit (not shown). The synchronization unit may be comprised in the control unit 9, or it may be apart. The PSG 17, the PSA 19, the video camera 21, and the display may be synchronized. Preferably, the synchronization is implemented electronically.

Figure 6:
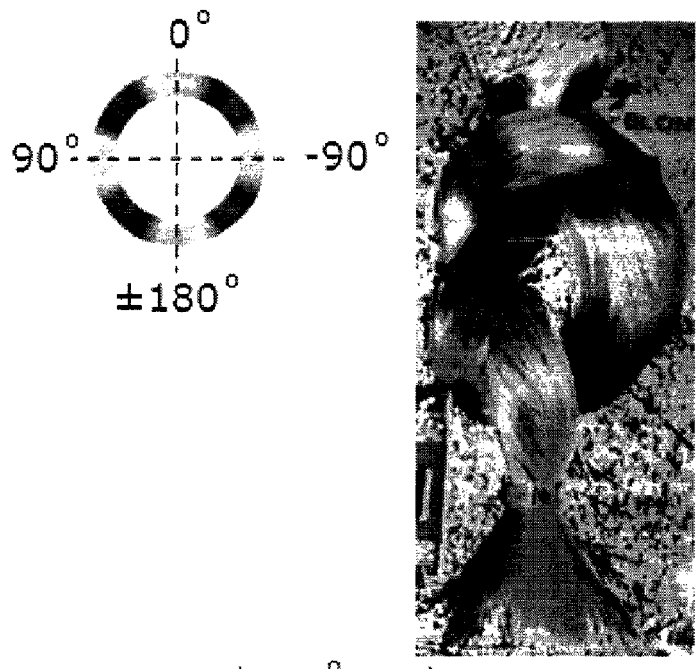
FIG. 6 shows two examples of orientation images taken with the apparatus according to the present disclosure.
Figure 6:
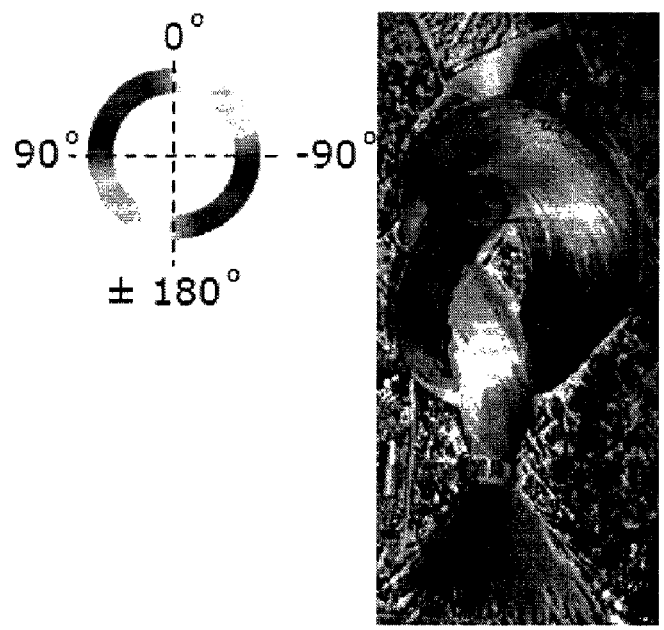

Referring now to FIG. 6, an example of color-coded orientation images indicating the orientation of the axes of the fibers is shown. In the upper image, 3≦N≦6, i.e., the π/2 ambiguity mentioned above remains. In the lower image, N≧6, i.e., there is no ambiguity concerning the value of the neutral axis' angle.

In the case that the birefringent fibers are human hair, in the visible spectrum, the internal reflection is always stronger in the red part of the spectrum for most hair types. In this spectrum range, black hair has a strong attenuation and therefore, only few internal reflection is observed. The lighter the hair is (from dark to red to brown to gray to blond to bleached hair to transparent white fiber), the more internal reflection there is. Therefore, working in the visible part of the spectrum may be suitable for measurements on light samples or on dark samples having a strong signal of internal reflection (for example, reflections on a curl).

Working in the NIR range (>750 nm) may be suitable to measure the orientation of hair fibers because the attenuation is lower for all hair types and especially black hair in this part of the spectrum, which results in a large modulation of the internal reflection.

Depending on the kind of light source and the characteristics thereof, different realization examples of the apparatus according to the present disclosure may be considered. For example, an apparatus using a cw laser source or LEDs may be used in the laboratory where it is possible to work in a dark environment. Further, a field system would rather employ a pulsed or flashed light source to make it more suitable for working in a normal environment presenting background light of which the acquisition needs to be minimized. The choice of a laboratory or a field system also depends on the polarizers comprised by the PSG and the PSA and their switching times.

Advantageously, apparatus and method of the present disclosure may provide at least one of the following advantages. The laboratory system is easy to implement and all the elements of the apparatus as well as the image acquisition can be controlled by the control unit, for example a personal computer. The field system allows for a very fast image acquisition and output. In either case, neither knowledge nor assumptions about the fiber orientation are needed, i.e., the fibers may be mutually randomly organized.

The method and apparatus according to the present disclosure may be implemented with several applications. For example, the growth, the homogeneity or the degree of curliness of human hair may be visualized. The effect of styling products (i.e., holding power, freeze control) on the hair may also be studied and subjected to the opinion of a customer jury.

Further, the orientation determination method may be implemented to assist 3D rendering of hair or other birefringent fibers, for example for video games and animation movies.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

What is claimed is:

1. A method to determine an orientation of randomly arranged birefringent fibers, the method comprising:
   emitting light;
   creating $N_i$ polarization states of the emitted light;
   illuminating the birefringent fibers with the emitted light so polarized;
   generating $IR_i$ internal reflection components of the light in the birefringent fibers;
   observing the light from the illuminated birefringent fibers;
   creating $O_i$ polarization states of the observed light;
   forming $I_i$ images of the observed polarized light, each image comprising an information ($N_i$, $O_i$, $IR_i$) wherein i=1, 2, . . . n and n≧3;
   separating the i-th internal reflection component from the i-th image; and
   calculating an angle of a neutral axis of the birefringent fibers using the internal reflection components.

2. The method according to claim 1, wherein the birefringent fibers comprise at least one of textile fibers and hair.

3. The method according to claim 1, wherein the wavelength of the emitted light is in the near infrared range.

4. The method according to claim 1, wherein the wavelength of the emitted light is in the visible range.

5. The method according to claim 1, wherein the i-th polarization state of the emitted light and the i-th polarization state of the observed light are the same.

6. The method according to claim 1, wherein the i-th polarization state of the emitted light is different from the i-th polarization state of the observed light.

7. The method according to claim 1, wherein the calculating comprises performing a Fourier transform on the $IR_i$ internal reflection components in each pixel of the $I_i$ images.

8. An apparatus to determine an orientation of randomly-arranged birefringent fibers, comprising:
   a light source to emit light;
   a first variable polarizer to create $N_i$ polarization states of the emitted light, the emitted light so polarized being indented to illuminate the birefringent fibers, thereby generating $IR_i$ internal reflection components of the light in the birefringent fibers;
   a detector to observe the light from the illuminated birefringent fibers;
   a second variable polarizer to create $O_i$ polarization states of the observed light;
   wherein the detector forms $I_i$ images of the observed polarized light, each image comprising an information ($N_i$, $O_i$, $IR_i$), wherein i=1, 2, . . . , n and n≧3;
   an image processing unit to separate the i-th internal reflection component from the i-th image; and
   a processor to calculate an angle of a neutral axis of the birefringent fibers using the $IR_i$ internal reflection components.

9. The apparatus according to claim 8, wherein the light source comprises a pulsed laser source.

10. The apparatus according to claim 8, wherein the light source comprises a cw laser source.

11. The apparatus according to claim 8, wherein the light source comprises at least one light emitting diode.

12. The apparatus according to claim 8, wherein the light source comprises a flash lamp.

13. The apparatus according to claim 8, wherein the detector comprises a video camera.

14. The apparatus according to claim 8, wherein each one of the first and the second variable polarizers are one of actively and passively controlled.

15. The apparatus according to claim 8, wherein the first and the second variable polarizers are incorporated in a single polarizer.

16. The apparatus according to claim 8, wherein the image processing unit and the processor are incorporated in a computer.

17. The apparatus according to claim 8, further comprising a synchronization unit configured to synchronize the first and second variable polarizers and the detector.

* * * * *